United States Patent [19]

Finger

[11] Patent Number: Plant 6,651

[45] Date of Patent: Mar. 7, 1989

[54] KALANCHOE PLANT NAMED CAPRICE

[75] Inventor: Hermann Finger, Wiesmoor, Fed. Rep. of Germany

[73] Assignee: Wiesmoor-Gartnerie und Baumschule GmbH, Wiesmoor, Fed. Rep. of Germany

[21] Appl. No.: 108,986

[22] Filed: Oct. 16, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Kalanchoe plant named Caprice, having flowers which are salmon orange when opening and turn to a light pink on maturity, good basal branching, vigorous and compact growth habit, full and branched flower cluster, and its excellent keeping quality.

1 Drawing Sheet

The present invention relates to a new and distinctive cultivar of Kalanchoe plant, botanically known as *Kalanchoe blossfeldiana,* and known by the cultivar name Caprice. Caprice was developed by me in Wiesmoor, Federal Republic of Germany by crossing Seraya (U.S. Plant Pat. No. 5,362), the seed parent, with Fortyniner (U.S. Plant Pat. No. 5,256), the pollen parent.

Asexual reproduction of Carpice by me in Wiesmoor, Federal Republic of Germany of stem cuttings taken from a selection from the progeny of the stated cross has shown that the unique features of this new Kalanchoe are stabilized and are reproduced true to type in successive propagations.

The following characteristics distinguish the new Kalanchoe from both its parent varieties and other cultivated Kalanchoes of this type known and used in the floriculture industry:

1. The flowers of Caprice when opening are salmon orange, maturing to a light pink. By contrast, Seraya (U.S. Plant Pat. No. 5,362) is a slamon pink, Fortyniner (U.S. Plant Pat. No. 5,256) is a yellow, Citation (U.S. Plant Pat. No. 5,533) is a deeper pink,and Dignity (U.S. Plant Pat. No. 5,255) is a lavender pink.

2. Flower size is similar to Citation, with Seraya, Fortyniner and Dignity all having large flowers. All cultivars have rounded petals.

3. Caprice has better basal branching than either parent and Citation and Dignity, but not as good as Charme, a cultivar of applicant disclosed in a pending application.

4. Leaves of Caprice are dark green like Seraya, with Fortyniner, Dignity and Citation all having more yellow-green leaves.

5. The crenate pattern on the leaf margin is intermediate between the deep cuts of Seraya and the shallow cuts of Fortyniner, and the patterns more cut than Dignity and Citation.

6. Leaf size is similar to Charme and Fortyniner, with Seraya, Citation and Dignity having larger leaves.

7. Plants of Caprice are compact like Charme, with Fortyniner, Citation, Dignity and Seraya all having a more upright, taller, open growth habit.

8. Flower cluster is very full and branched, not quite as full as Charme. Dignity, Fortyniner, Citation and Seraya all have more open, less full flower clusters.

9. Caprice is similar in maturity to all the other comparison cultivars but due to the full flower cluster appears earlier to all except Charme.

10. Caprice has better keeping quality than Fortyniner and similar keeping qualities to Seraya, Citation, Charme and Dignity.

The accompanying colored photograph illustrates in top perspective view the overall appearance of Caprice, with colors being as true as it is reasonably possible to obtain in a colored reproduction of this type.

The following is a detailed description of my new Kalanchoe variety based on plants produced under commercial practices in Wiesmoor, Federal Republic of Germany and Ashtabula, Ohio. Color references are made to The Royal Horticultural Society Colour Chart, except where general colors of ordinary dictionary significance are used.

Parentage: A controlled cross between the female parent Seraya and the male parent Fortyniner.

Propagation:

(A) *Type cutting.*—2 cm long stem cutting.

(B) *Time to root.*—10 days at 21° C. summer. 14 days at 21° C. winter.

(C) *Rooting habit.*—Abundant; fine, fibrous roots.

Plant description:

(A) *Form.*—Compact, upright, growth with flowers above foliage, with good basal branching resulting in a full symmetrical plant. Growing and scheduling practices can produce a small plant in a 10 cm pot or a larger plant in a 12 cm pot.

(B) *Habit of growth.*—Vigorous grower with shoots forming at every node. Has short internodes which result in plant being dense and having flowers on the upper two-thirds of the plant.

(C) *Foliage.*—Leaves simple, opposite. (1) Size: A full grown leaf of a flowering plant in a 10 cm pot is 90 mm long and 60 mm wide. (2) Shape: Oblong to ovate, apex obtuse, base acute. (3) Texture: Glabrous, succulent, coriaceous. (4) Margin: Pronounced crenate. (5) Color: Young foliage, top side 137A, under side 137C. Mature foliage, top side 137B, under side 147B.

Flowering description:

(A) *Flowering habits.*—Inflorescence is a cyme with the terminal flower of the main axis opening first, followed by terminal flowers of the side branches and continuing with subsequent development of branches in the inflorescence.

(B) *Natural flowering season.*—Early January. Flowering time under controlled daylength at 20° C. in summer is 11 weeks; in winter 13 weeks. Flowering time depends on temperature, light intensity and other growing conditions.

(C) *Flower buds.*—Elliptical to oblong, up to 8 mm long, developing to tubular as flower petals mature, sheathed with four green sepals; corolla at maturity is 5 mm long.

(D) *Flowers borne.*—On compound dichasial cymes, primary peduncle 3 mm in diameter, but varying in length based on environment and B-9 application. Pedicles are up to 5 mm long.

(E) *Quantity of flowers.*—Highly floriferous; plant is well branched, the branches developing flower clusters commonly having 200 plus flowers in the total flower cluster.

(F) *Petals.*—(1) Shape: Almost round, top cuspidate. (2) Color: Top side, when opening, 29B, fading to 37C and then to 55C; under side 29B to 55C. (3) Number of petals: 4.

(G) *Reproductive organs.*—(1) Stamens: Eight (8) in number. (a) Anther shape: Flat, elliptical, color yellow. (b) Filament color: Light green. (c) Pollen color: Yellow. (2) Pistils (a) Stigma shape: Flat, color light green. (b) Style color: Light green. (c) Ovaries: 4 in number, size 5 mm, color green.

Disease resistance: No disease observed to date.

Other important characteristics: Caprice has shown tolerance to heat delay of flowering under black shade cloth when short day treatment is applied during high temperature periods. Flowers that open as a salmon orange and fade to a light pink provide a pleasant color combination. Caprice is an excellent 10 cm pot cultivar.

I claim:

1. A new and distinct cultivar of Kalanchoe plant named Caprice, as illustrated and described.

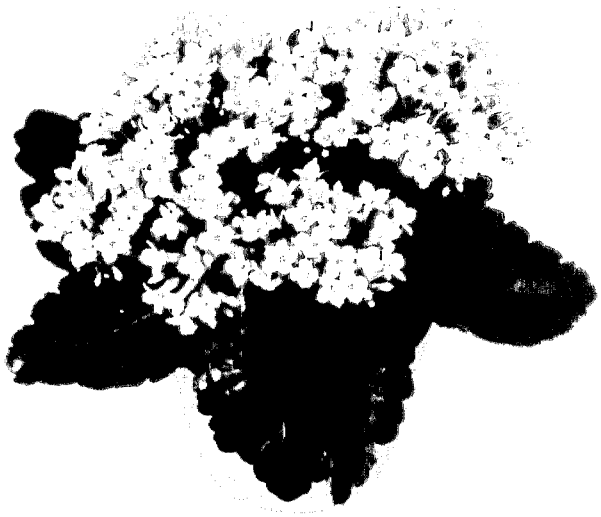

* * * * *